United States Patent
Flynn et al.

[11] Patent Number: 6,141,594
[45] Date of Patent: Oct. 31, 2000

[54] SINGLE PASS LEAD AND SYSTEM WITH ACTIVE AND PASSIVE FIXATION ELEMENTS

[75] Inventors: David M. Flynn, Lino Lakes; Carol Werlein, Ham Lake, both of Minn.

[73] Assignee: Cardiac Pacemakers, Inc., St. Paul, Minn.

[21] Appl. No.: 09/121,005

[22] Filed: Jul. 22, 1998

[51] Int. Cl.$^7$ ............................................. A61N 1/05
[52] U.S. Cl. ................... 607/127; 607/122; 607/123; 607/126; 600/375; 600/374
[58] Field of Search ........................ 607/123, 122, 607/126, 127, 120; 600/374, 375

[56] References Cited

U.S. PATENT DOCUMENTS

| | | | |
|---|---|---|---|
| 4,289,144 | 9/1981 | Gilman | 607/123 |
| 4,497,326 | 2/1985 | Curry | 607/123 |
| 4,549,548 | 10/1985 | Wittkampf et al. | |
| 4,567,901 | 2/1986 | Harris | 607/123 |
| 4,608,986 | 9/1986 | Beranek et al. | 607/123 |
| 4,643,201 | 2/1987 | Stokes | 607/122 |
| 4,693,258 | 9/1987 | Osypka et al. | 128/783 |
| 4,827,940 | 5/1989 | Mayer et al. | 600/377 |
| 4,932,969 | 6/1990 | Frey et al. | 623/17 |
| 5,217,028 | 6/1993 | Dutcher et al. | 128/785 |
| 5,466,253 | 11/1995 | Doan | 607/122 |
| 5,476,497 | 12/1995 | Mower et al. | 607/122 |
| 5,628,779 | 5/1997 | Bornzin et al. | 607/123 |
| 5,674,272 | 10/1997 | Bush et al. | 607/122 |
| 5,769,881 | 6/1998 | Schroeppel et al. | 607/123 |

FOREIGN PATENT DOCUMENTS

| | | | |
|---|---|---|---|
| 452278A2 | 4/1990 | European Pat. Off. | A61N 1/05 |
| 2575925 | 7/1986 | France | 607/127 |
| 94/22525 | 4/1993 | WIPO | A61N 1/05 |

*Primary Examiner*—Kennedy Schaetzle
*Attorney, Agent, or Firm*—Schwegman, Lundberg, Woessner & Kluth, P.A.

[57] ABSTRACT

A single pass endocardial lead is provided which is adapted for implantation on or about the heart and for connection to a system for monitoring or stimulating cardiac activity. The lead includes a main body which extends into two distal leg portions, each having at least two electrodes coupled therewith. The first leg is for positioning within the ventricle of the heart. The second leg is for positioning within the atrium of the heart. Both the first leg and the second leg are bipolar and are adapted for positioning and fixation to the heart wall. The first and second legs can be fixated to the heart wall using either passive or active fixation structures. A movement assembly for advancing a helix comprises an externally threaded collar which engages with an internally threaded housing or housing insert.

31 Claims, 9 Drawing Sheets

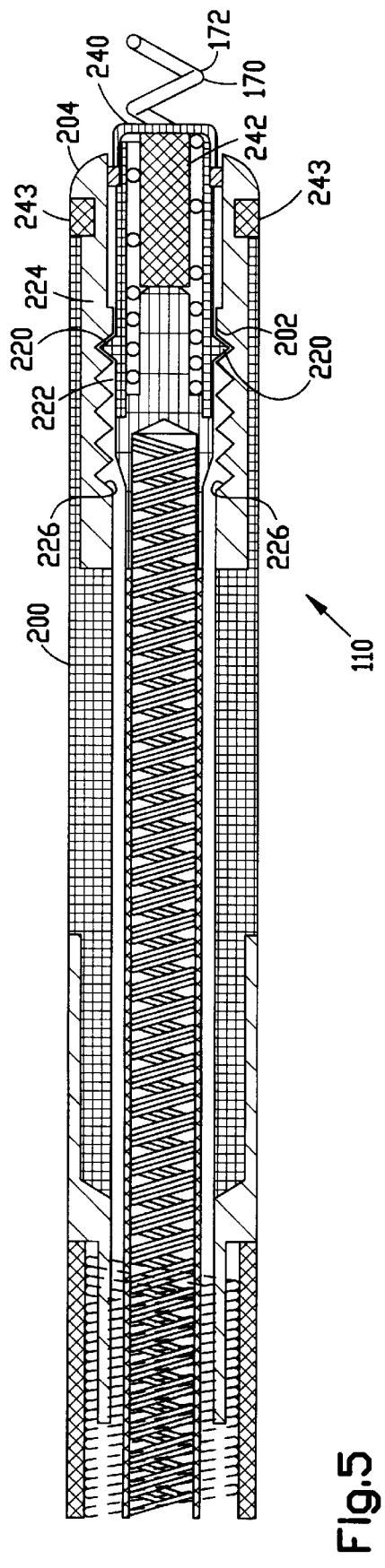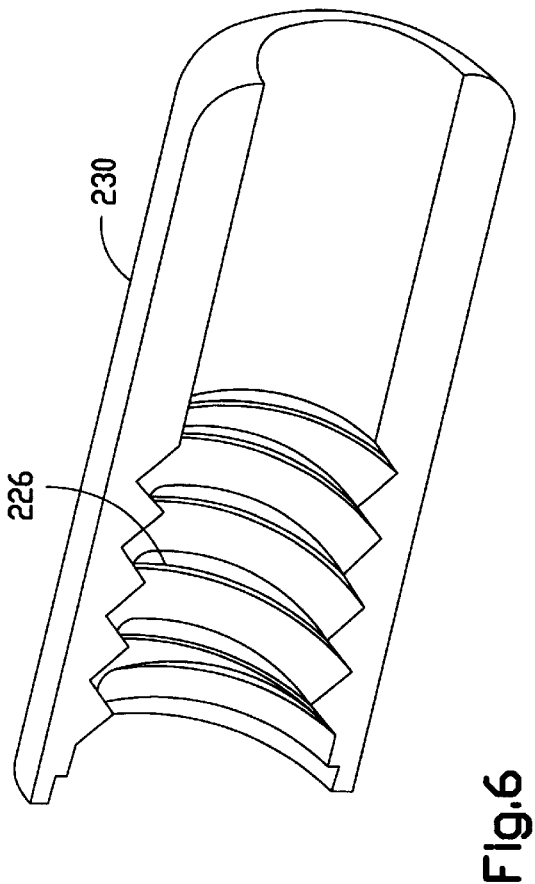

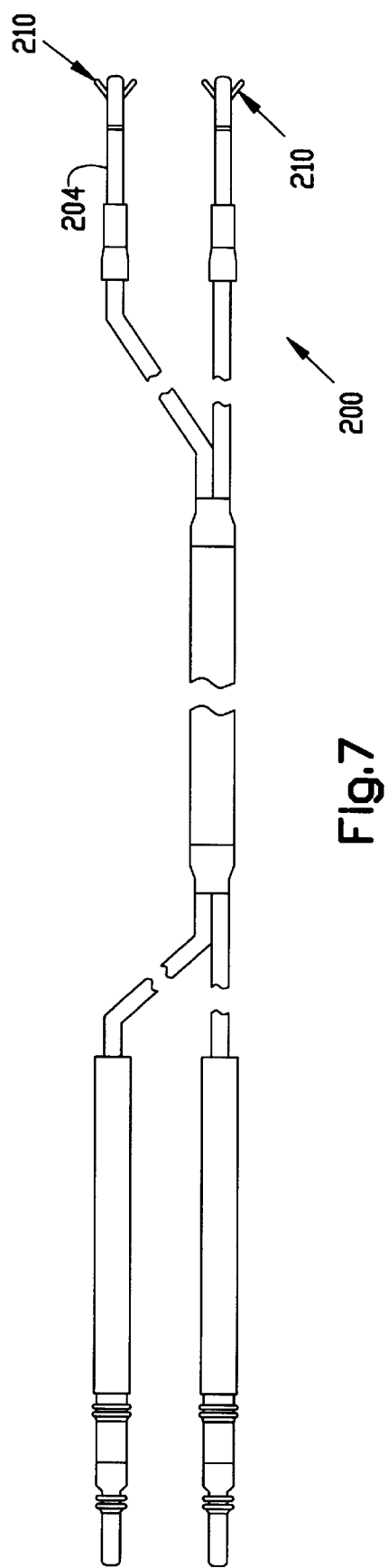

SINGLE PASS LEAD AND SYSTEM WITH ACTIVE AND PASSIVE FIXATION ELEMENTS

FIELD OF THE INVENTION

The present invention relates generally to implantable leads. More particularly, it pertains to a single lead which can simultaneously pace, sense, and/or defibrillate two chambers of the heart.

BACKGROUND OF THE INVENTION

Electrodes implanted in or about the heart have been used to reverse (i.e., defibrillate or cardiovert) certain life threatening arrhythmias, or to stimulate contraction of the heart, where electrical energy is applied to the heart via the electrodes to return the heart to normal rhythm. Electrodes have also been used to sense and deliver pacing pulses to the atrium and ventricle. The electrode in the atrium senses the electrical signals that trigger the heartbeat. The electrode detects abnormally slow (bradycardia) or abnormally fast (tachycardia) heartbeats. In response to the sensed bradycardia or tachycardia condition, a pulse generator produces pulses or signals to correct the condition. The same node used to sense the condition is also used in the process of delivering a corrective pulse or signal from the pulse generator of the pacemaker.

There are four main types of pulses which are delivered by a pulse generator. Two of the signals or pulses are for pacing the heart. First of all, there is a pulse for pacing the heart when it is beating too slowly, and the pulse triggers the heart beat. The pulses are delivered at a rate to increase the heart rate to a desired level. The second type of pacing, called antitachycardia pacing, is used on a heart that is beating too fast. In antitachycardia pacing, the pacing pulses are delivered initially at a rate faster than the beating heart. The rate of the pulses is then slowed until the heart rate is at a desired level. The third and fourth type of pulses are used when the heart is beating too fast and the heart is fibrillating. The third type is called cardioversion. This is delivery of a relatively low energy shock, typically in the range of 0.75 to 1 joule, to the heart. The fourth type of pulse or signal is a defibrillation signal which is the delivery of a high energy shock, typically up to 34 joules, to the heart.

Sick sinus syndrome and symptomatic AV block constitute the major reasons for insertion of cardiac pacemakers today. Cardiac pacing may be performed by the transvenous method or by electrodes implanted directly onto the epicardium, where transvenous pacing may be temporary or permanent. In temporary transvenous pacing, an electrode lead is introduced into a peripheral vein and fluoroscopically positioned against the endocardium. The external terminals of the leads are connected to an external cardiac pacemaker which has an adjustable rate and milliamperage control. Temporary transvenous pacing is utilized prior to insertion of a permanent pacing system and in situations in which the indication for pacing is judged to be reversible (drug-induced AV block or bradycardia) or possibly irreversible and progressive (AV and bundle branch blocks associated with myocardial infarction).

Permanent transvenous pacing systems are implanted under sterile surgical conditions. An electrode lead is generally positioned in the right ventricle and/or in the right atrium through a subclavian vein, and the proximal electrode terminals are attached to a pacemaker which is implanted subcutaneously. Some patients require a pacing system to correct an abnormally slow heart (bradycardia condition) as well as a defibrillation system to detect when the heart starts beating abnormally fast (tachycardia condition) and to defibrillate or deliver a pulse to the heart to correct the abnormally fast heartbeat. In the past, a common practice for a patient having both of these conditions would be to provide two different leads attached to the heart. One would be implanted for delivering pacing signals to the heart to correct for the bradycardia condition. A separate lead would be implanted to sense a fast beating heart and defibrillate the heart to correct for the tachycardia condition. One lead is placed in the atrium and the other lead is placed in the ventricle.

Having two separate leads implanted within the heart is undesirable for many reasons. Among the many reasons are that the implantation procedure for implanting two leads is more complex and also takes a longer time when compared to the complexity and time needed to implant a single lead. In addition, two leads may interact with one another after implantation or in vivo which can result in dislodgment of one or both of the leads. In vivo interaction may also cause abrasion of the insulative layer along the lead which can result in an electrical failure of one or both of the leads. Another problem is that as more leads are implanted in the heart, it can become increasingly difficult to add additional leads. Two separate leads also increase the risk of infection and may result in additional health care costs associated with implantation and follow-up.

Because of these problems, a single lead, called a single pass lead design, having electrodes for both pacing and sensing in both chambers of the heart has been used. One drawback of some current single pass lead designs is that they use "floating" electrodes or electrodes which are not attached to the endocardial wall of the heart. The floating electrodes lay in the blood pool or against the endocardial wall of the heart and the electrode may move slightly within the heart. The electrode positioned within the atrium of a single-pass endocardial lead generally is an electrically conductive cylindrical ring or semicylindrical ring structure, which does not allow for tissue ingrowth into the electrode. Since the location of the electrodes is not fixed with respect to the atrial wall, the electrical performance of these electrodes varies and is generally less than optimal. Both the electrical sensing capability as well as the pacing delivery capability of such electrodes are suboptimal. The pacing parameters of such a floating electrode are also suboptimal. In addition, the floating electrodes can require increased voltage which unnecessarily drains the battery.

Some atrial leads have passive fixation elements that affix to the atrium over time. One example of a single pass lead is shown in U.S. Pat. No. 4,289,144 issued to Gilman on Sep. 15, 1981. Gilman relates to an atrial-ventricular pacing lead having outwardly extending tines surrounding the ventricular lead electrode and/or the outer atrial lead electrode. Another example is shown in U.S. Pat. No. 4,643,201 issued to Stokes on Feb. 17, 1987 which titled "Single-Pass A-V Lead." Stokes relates to a ventricular lead branch which has excess length adapted for a larger heart and an atrial lead branch having a "J" shape. A problem with these leads is that the electrodes are much more likely to be displaced from the wall of the atrium. When the electrodes are placed far from the wall, there can be detrimental effects. For example, the electrode may be unable to sense a tachycardia condition. Another example might be that signals for pacing may be ineffective. Additional power may have to be used to pace the heart thereby depleting energy from the battery of the pulse generator of the pacing system.

There is a real need for a single-pass endocardial pacing lead that has improved fixation to the wall of the atrium of the heart. A single-pass lead equipped with such an electrode would allow for better sensing capability and better pacing delivery to the heart. In addition, there is a need for a single-pass lead having an electrode for positioning within the atrium that allows for tissue ingrowth. Tissue ingrowth further enhances the electrical performance of the electrode. In addition, the lead and electrode is further stabilized within the heart as a result of tissue ingrowth.

SUMMARY OF THE INVENTION

A single-pass endocardial lead is provided which is adapted for implantation on or about the heart and is adapted for connection to a system for monitoring or stimulating cardiac activity and includes a lead body. The lead extends from two terminal legs at a proximal end of the lead to two electrode legs at a distal end of the lead. Each electrode leg includes a first electrode and a second electrode. The second electrode is adapted for positioning and fixation to the wall of the atrium of the heart.

In one embodiment, a bifurcated lead includes a main lead body which is adapted to carry signals to and from the heart. The main body extends to a first electrode assembly which has a first electrode and a second electrode, and is adapted to be implanted within a first chamber of the heart. The body also extends to a second electrode assembly which has a third electrode and a fourth electrode, and is adapted to be implanted within a second chamber of the heart. In another embodiment, the lead body has an intermediate portion which comprises a quad lumen body. In yet another embodiment, the first electrode leg and the second electrode leg each have a semi-circular profile. A yoke, in another configuration, couples the first electrode leg and the second electrode leg with the intermediate portion. The first electrode assembly and the second electrode assembly can be either actively or passively fixated within the heart. A mesh screen can also be provided to allow for better tissue in-growth.

In another embodiment, a bifurcated lead includes a main lead body which is adapted to carry signals to and from the heart. The main body extends to a first electrode assembly which has a first electrode and a second electrode, and is adapted to be implanted within a first chamber of the heart. The body also extends to a second electrode assembly which has a third electrode and a fourth electrode, and is adapted to be implanted within a second chamber of the heart. The first electrode assembly and the second electrode assembly include an active fixation portion, to which a movement assembly is coupled. In one embodiment, the movement assembly includes an externally threaded portion which is engaged with an internally threaded housing. In another embodiment, the internally threaded portion comprises an insert disposed within the lead.

In another embodiment, a bifurcated lead includes a main lead body which is adapted to carry signals to and from the heart. The main body extends to a first electrode assembly which has a first electrode and a second electrode, and is adapted to be implanted within a first chamber of the heart. The body also extends to a second electrode assembly which has a third electrode and a fourth electrode, and is adapted to be implanted within a second chamber of the heart. The lead is coupled with a signal generator which is adapted for producing pulses to apply to the heart.

Advantageously, the bi-polar single pass lead allows for two chambers of the heart to be paced and/or sensed, while only one lead is implanted within the patient. This assists in preventing added stress and expense for the patient. In addition, the active fixation element will not hook nor snag tissue when it is retracted within the lead. The active fixation element does not require the use of a stylet, since the terminal pins are used to extend and retract the active fixation element. An additional benefit is that only one lead is placed into the patient for both sensing and pacing, thereby eliminating the need for placement of the second lead.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

BRIEF DESCRIPTION OF THE DRAWINGS

FIG. 5 is a cross-section view taken along 5—5 of FIG. 1 illustrating a single-pass lead constructed in accordance with one embodiment of the present invention.

FIG. 6 is a perspective view illustrating a movement assembly of the lead constructed in accordance with one embodiment of the present invention.

FIG. 7 is a side elevational view illustrating a single-pass lead constructed in accordance with another embodiment of the present invention.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1A:
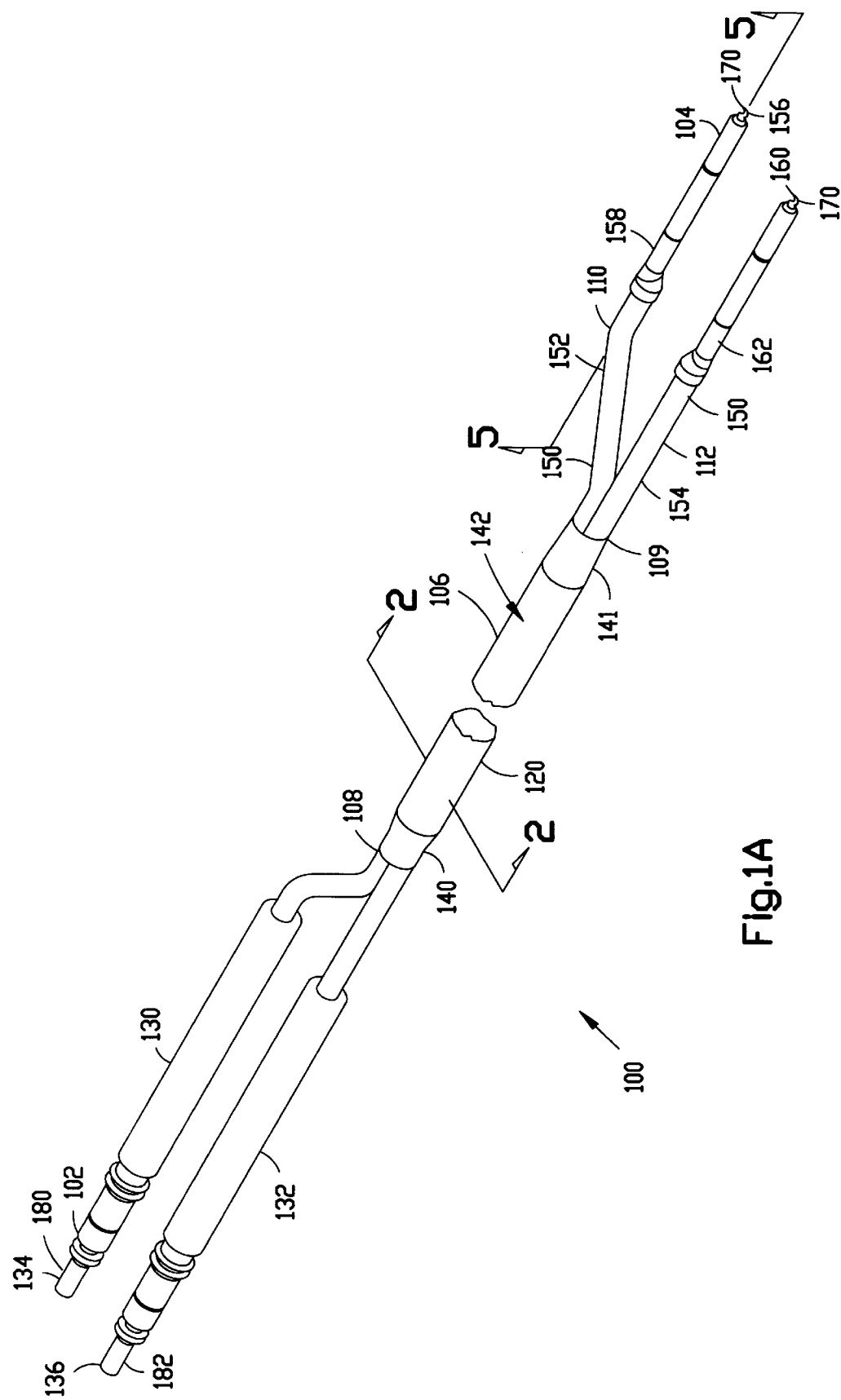
FIG. 1A is a first perspective view illustrating a single-pass lead constructed in accordance with one embodiment of the present invention.
Figure 9:
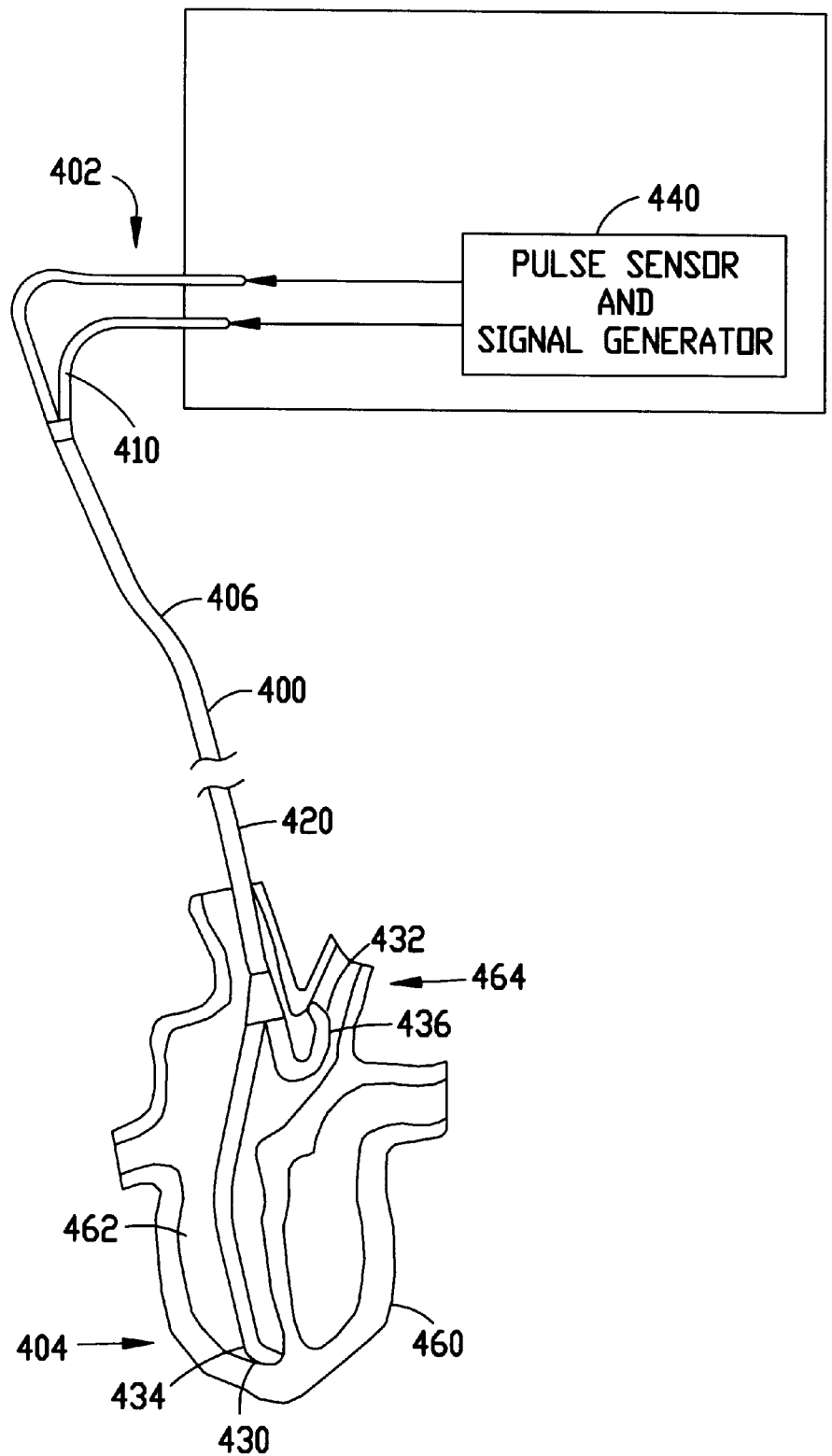
FIG. 9 is a block diagram illustrating a system for delivering signals to the heart constructed in accordance with one embodiment of the present invention.

FIG. 1A illustrates a lead 100 for delivering electrical pulses to stimulate the heart. The lead 100 extends from a proximal end 102 to a distal end 104 and comprises a first and second connector terminal 180, 182 near the proximal end 102. The lead 100 also includes a lead body 120, a first electrode assembly 110, and a second electrode assembly 112, as will be further described below. The connector terminals 180, 182 electrically connect the various electrodes and conductors with the lead body to a pulse sensor and generator (FIG. 9). The pulse sensor and generator (FIG. 9) contain electronics to sense various pulses of the heart and also produce pulsing signals for delivery to the heart. The pulse sensor and generator also contain electronics and software necessary to detect certain types of arrhythmias and to correct for them. Physicians are able to program the pulse sensor and generator to correct a particular arrhythmia that the patient may have. Numbers types of connector terminals which connect to a pulse sensing and generating unit can be used. In one embodiment, the connector terminals 180, 182 are designed to conform with International Standards.

The lead body 120, in one embodiment, is formed from a polymer biocompatible material, and can include tubing made from a silicone rubber polymer. The lead body 120 extends from the proximal end 102 of the lead 100 to the distal end 104 of the lead 100, and has an intermediate portion 106 therebetween. Near the proximal end 102 of the lead body 120, the lead body 120 has at least two IS1 terminal legs, including a first terminal leg 130 and a second terminal leg 132.

At the proximal end 102 of the first terminal leg 130 and the second terminal leg 132 are terminal pins 134, 136 which can be operatively coupled with a pulse sensor and signal generator, as discussed above. In one embodiment, the terminal pins 134, 136 are used to rotate the active fixation device, discussed further below. In another embodiment, a stylet driven mechanism is used to rotate the active fixation device. The first terminal leg 130 and the second terminal leg 132 extend from the terminal pins 134, 136 of the proximal end 102 of the lead 100 to the intermediate portion 106 of the lead 100, where the first terminal leg 130 and the second terminal leg 132 are coupled with the intermediate portion 106 at a proximal bifurcation point 108. In one embodiment, the first terminal leg 130 and the second terminal leg 132 are coupled with the intermediate portion 106 with a yoke 140 which operates as a strain relief. The yoke 140, in one embodiment, comprises a sheath for covering at least portions of the first and second terminal legs 130, 132 and the intermediate portion 106, where the sheath can be attached using medical adhesive or other attachment methods. In another embodiment, the yoke 140 is over-molded encompassing the intermediate portion 106 and the first and second terminal legs 130, 132.

Figure 1B:
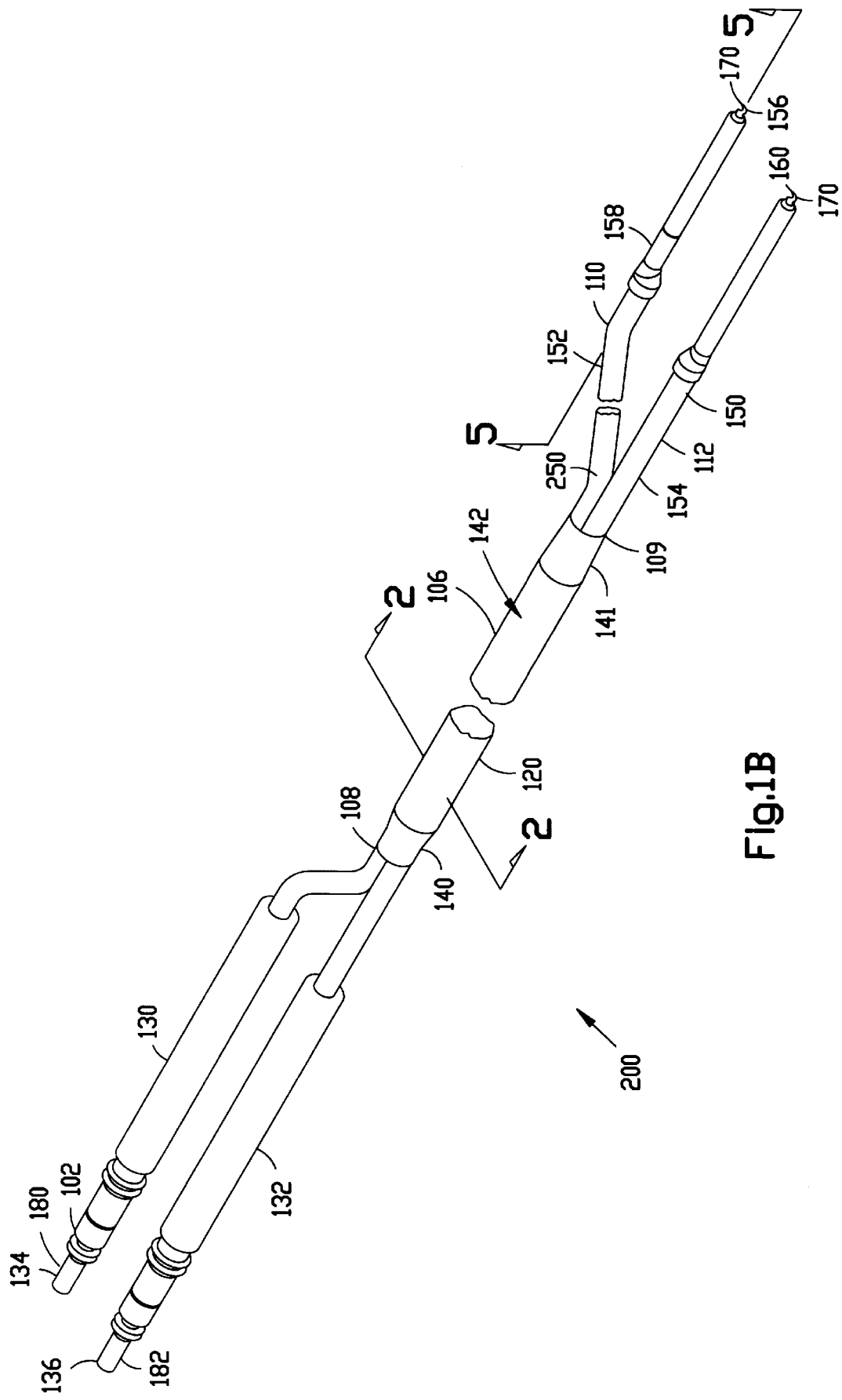
FIG. 1B is a second perspective view illustrating a single-pass lead constructed in accordance with one embodiment of the present invention.
Figure 2:
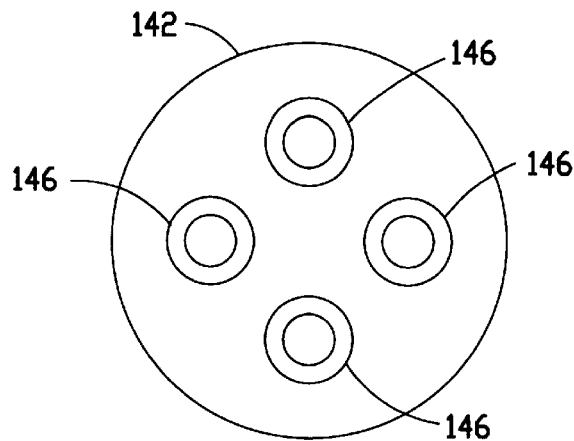
FIG. 2 is a cross-section view taken along 2—2 of FIG. 1A illustrating a single-pass lead constructed in accordance with another embodiment of the present invention.

The intermediate portion 106 of the lead body 120, as shown in FIG. 2, is comprised of quad-lumen tubing 142, which in one embodiment comprises PTFE insulation. Disposed within each lumen of the quad-lumen tubing 142 is a conductor 146, consisting of either a cable or a coil. Referring again to FIGS. 1A and 1B, the intermediate portion 106 extends from the proximal bifurcation point 108 to a distal bifurcation point 109. At the distal bifurcation point 109, in one embodiment, the intermediate portion 106 transitions into two bitumen tubes 150, including a first electrode leg 152 and a second electrode leg 154. The first electrode leg 152, in one embodiment, is shorter in length than the second electrode leg 154, where the first electrode leg 152 is for implantation into an atrium (not shown) and the second electrode leg 154 is for implantation within the ventricle (not shown). In another embodiment, the first electrode leg 152 and the second electrode leg 154 are coupled with the intermediate portion 106 with a yoke 141, similar to the yoke 140 discussed above. The first electrode leg 152 and the second electrode leg 154 each extend to the first electrode assembly 110 and the second electrode assembly 112, respectively.

In one embodiment, as shown in FIG. 1A, the first electrode assembly 110 and the second electrode assembly 112 are both bipolar. In another embodiment, as shown in FIG. 1B, the first electrode assembly 110 is bipolar and the second electrode assembly 112 is unipolar. In yet another embodiment, similar to FIG. 1B, the first electrode assembly 110 is unipolar and the second electrode assembly 112 is bipolar. To form a unipolar electrode assembly, only a single conductor, discussed further below, is provided within the electrode assembly, and a single electrode is provided. The electrode, for either the bipolar or unipolar embodiments of the first and second electrode assemblies 110, 112, comprises a singular electrode or a combination of electrodes of the following: a tip electrode, a ring electrode, a defibrillator coil, or their equivalents. The various electrodes can be used for pacing, sensing, defibrillating, or a combination of the same.

In another embodiment, a first conductor set is disposed within the first electrode leg 152 and comprises a coil and a cable which terminate in a first pacing tip 156 and a first pacing ring 158, respectively. Similarly, as shown in FIG. 1A, a second conductor set is disposed within the second electrode leg 154 and comprises a coil and a cable which terminate in a second pacing tip 160 and a second pacing ring 162, respectively. For the embodiment shown in FIG. 1B, the second conductor set comprises only a second pacing tip 160, thereby forming a unipolar leg.

Figure 3A:
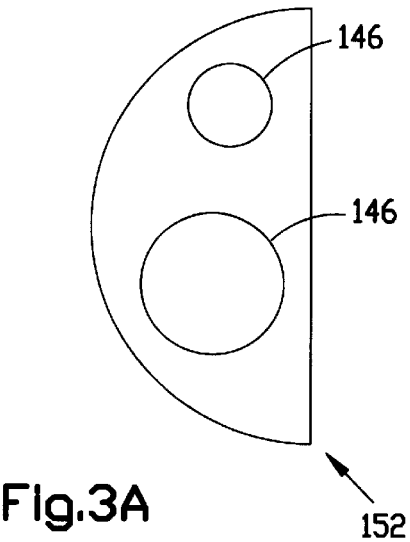
FIG. 3A is a cross-section view illustrating a portion of a single-pass lead constructed in accordance with yet another embodiment of the present invention.
Figure 4A:
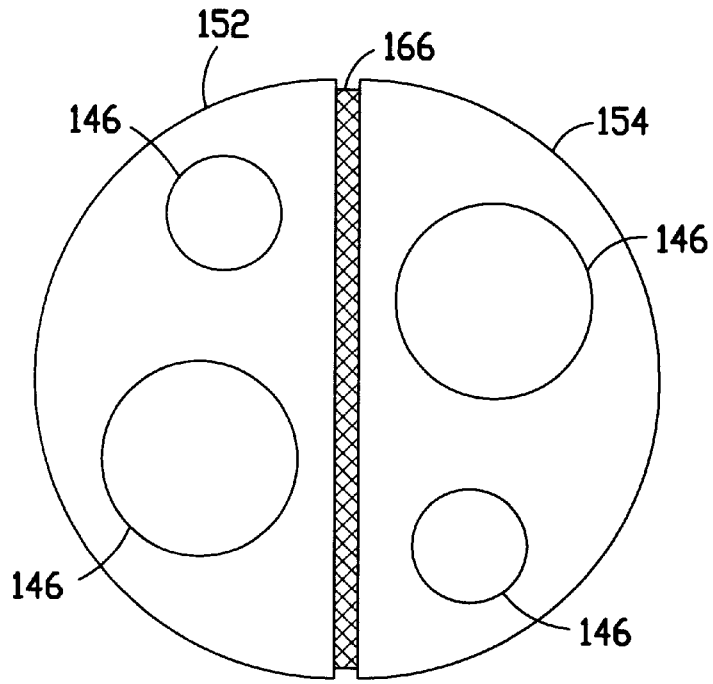
FIG. 4A is a cross-section view illustrating a portion of a single-pass lead constructed in accordance with one embodiment of the present invention.

The first electrode leg 152, in one embodiment, has a semi-circular cross-section, as shown in FIG. 3A. Similarly, the second electrode leg 154, in another configuration, also has a semi-circular cross-section. When placed adjacent to one another, the first electrode leg 152 and the second electrode leg 154 form a circular cross-section, as shown in FIG. 4A. In one configuration, medical adhesive or other equivalents 166, including dissolvable substances such as mannitol, are disposed between the first electrode leg 152 and the second electrode leg 154 to aid in the installation of the lead 100 within a patient.

Figure 3B:
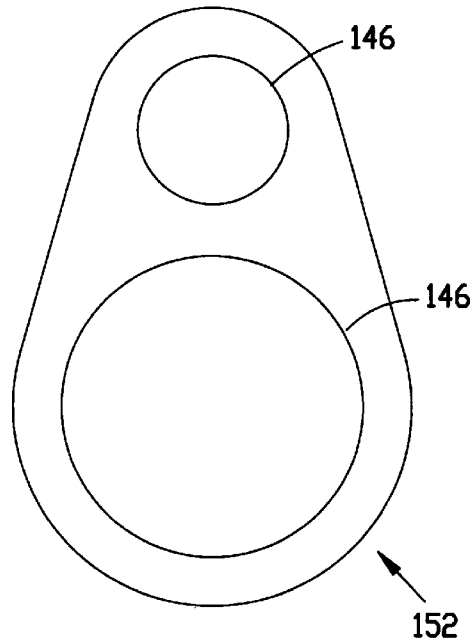
FIG. 3B is a cross-section view illustrating a portion of a single-pass lead constructed in accordance with one embodiment of the present invention.
Figure 4B:
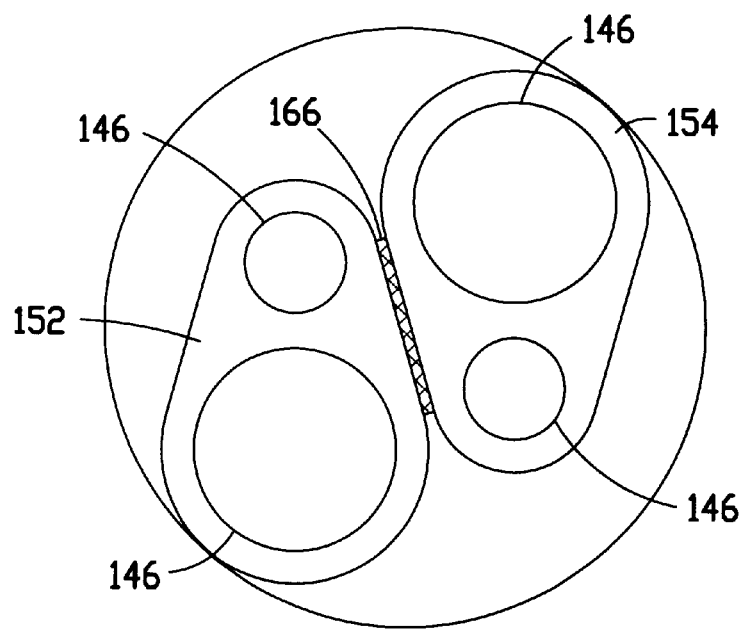
FIG. 4B is a cross-section view illustrating a portion of a single-pass lead constructed in accordance with one embodiment of the present invention.

Alternatively, the first electrode leg 152 has an elliptical cross-section, as shown in FIG. 3B. Similarly, the second electrode leg 154 has an elliptical cross-section. When placed adjacent to one another, the first electrode leg 152 and the second electrode leg 154 easily fit together, as shown in FIG. 4B. In another embodiment, medical adhesive or other equivalents 166, including dissolvable substances such as mannitol, are disposed between the first electrode leg 152 and the second electrode leg 154, as shown in FIG. 4B, to assist in the installation of the lead 100 within a patient. The cross-section of the first and second electrode legs 152, 154 are not limited to the above and can have other cross-sections.

In another configuration, the first electrode assembly 110 and the second electrode assembly 112 include an active fixation element 170, as shown in FIG. 1A. FIG. 5 illustrates the active fixation element 170 in greater detail. A lead 200 is provided extending to a distal end 204 which includes the active fixation element 170. The active fixation element 170, in one embodiment, comprises a helical screw 172.

In one configuration, the active fixation element 170 is retractable, which assists in avoiding injury to the patient during implantation. Alternatively, the active fixation element 170 rotates without translating along the lead 200. For this configuration, where the active fixation element 170 does not translate, a material, such as mannitol, is disposed about the active fixation element 170 to prevent snagging the interior of the vein as the lead 200 is positioned within the patient. The lead 200, in one embodiment, includes a movement assembly 202 which is adapted to transport the active fixation element 170. Alternatively, in another configuration, the distal end 204 of the lead 200 can include a passive fixation element 210, as shown in FIG. 7. The passive fixation element 210 in one configuration comprises a plurality of tines adjacent the distal end 204.

Referring again to FIG. 5, the movement assembly 202 includes external threads 220 associated therewith. In one configuration, the external threads 220 are disposed about a collar 222 of the lead 200. The external threads 220 are adapted to engage with internal threads 226 disposed within a housing 224 of the lead 200.

The external threads 220 provide a helical path for the internal threads 226. The movement assembly 202 is not, however, limited to the components described herein. For instance, the external threads 220 and the internal threads 226 can be provided on alternative components, and still be considered within the scope of the invention. In one configuration, an insert 230 is provided for the internal threads 226, as shown in FIG. 6. The insert 230 contains internal threads 226 which are adapted to engage with the external threads 220 of the collar 222. During use, the terminal pins 134, 136 (FIG. 1) are rotated which causes the collar 222 to rotate. As the collar 222 is rotated and the external threads 220 and the internals threads 226 engage, the active fixation element 170 moves along the axis 214 of the lead 200. The movement assembly 202 can be used with a wide variety of leads implementing active fixation, including, but not limited to, single pass dual chamber pacing leads, single pass dual chamber pacing/defibrillator leads, single chamber pacing leads, and single chamber pacing/defibrillator leads.

Referring again to FIG. 5, a mesh screen 240 is provided in another embodiment. The mesh screen 240 allows for better tissue in-growth, as well as enhanced sensing capabilities. The mesh screen 240 is disposed proximate to the active fixation element 170. In one embodiment, as the active fixation element 170 is translated and extended from the lead 200, mesh screen 240 moves with the active fixation element 170. The fixation element 170 engages the heart tissue and draws the mesh screen 240 into contact with the surface of the heart.

In another configuration, the lead 200 is provided with a medication distribution member which is adapted to release medicine after the lead 200 has been implanted into a patient. In one embodiment, the medication distribution member comprises a steroid plug 242 which is provided proximate to the mesh screen 240. The steroid plug 242 is located behind the mesh screen 240 relative to the heart. In another embodiment, the medication distribution member comprises a medication collar 243 to release drugs, such as a steroid medication. Drugs can be provided which prevent tissue inflammation after the electrode has been attached to the heart or which assist in blood clotting, or assist in providing other treatments.

Figure 8A:
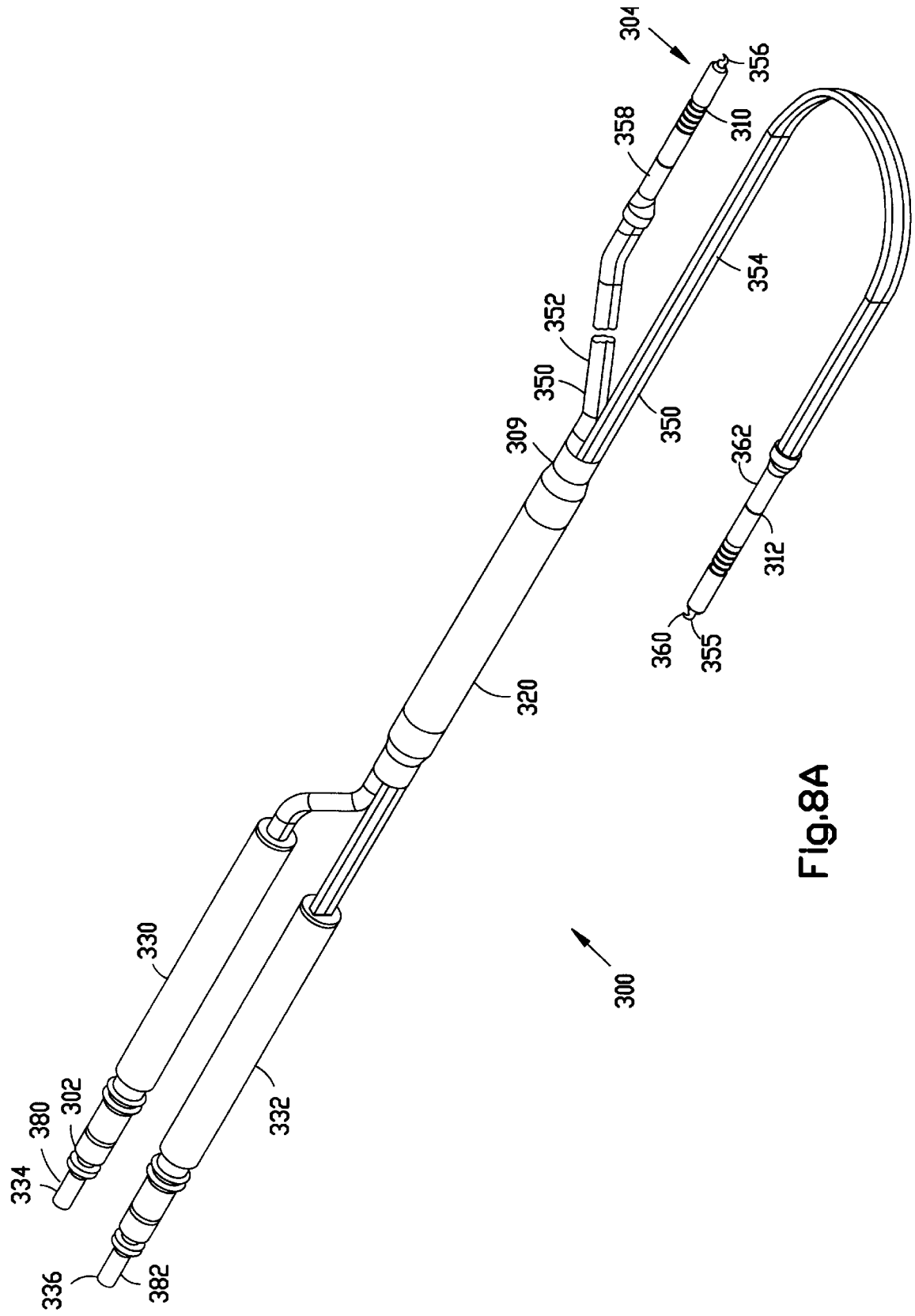
FIG. 8A is a first perspective view illustrating a single-pass lead constructed in accordance with one embodiment of the present invention.

FIG. 8A illustrates another embodiment showing the lead 300. The lead 300 extends from a proximal end 302 to a distal end 304 and comprises a first and second connector terminal 380, 382 near the proximal end 302. The lead 300 also includes a lead body 320, a first electrode assembly 310, and a second electrode assembly 312. Near the proximal end 302 of the lead body 320, the lead body 320 has at least two IS1 terminal legs, including a first terminal leg 330 and a second terminal leg 332.

Figure 8B:
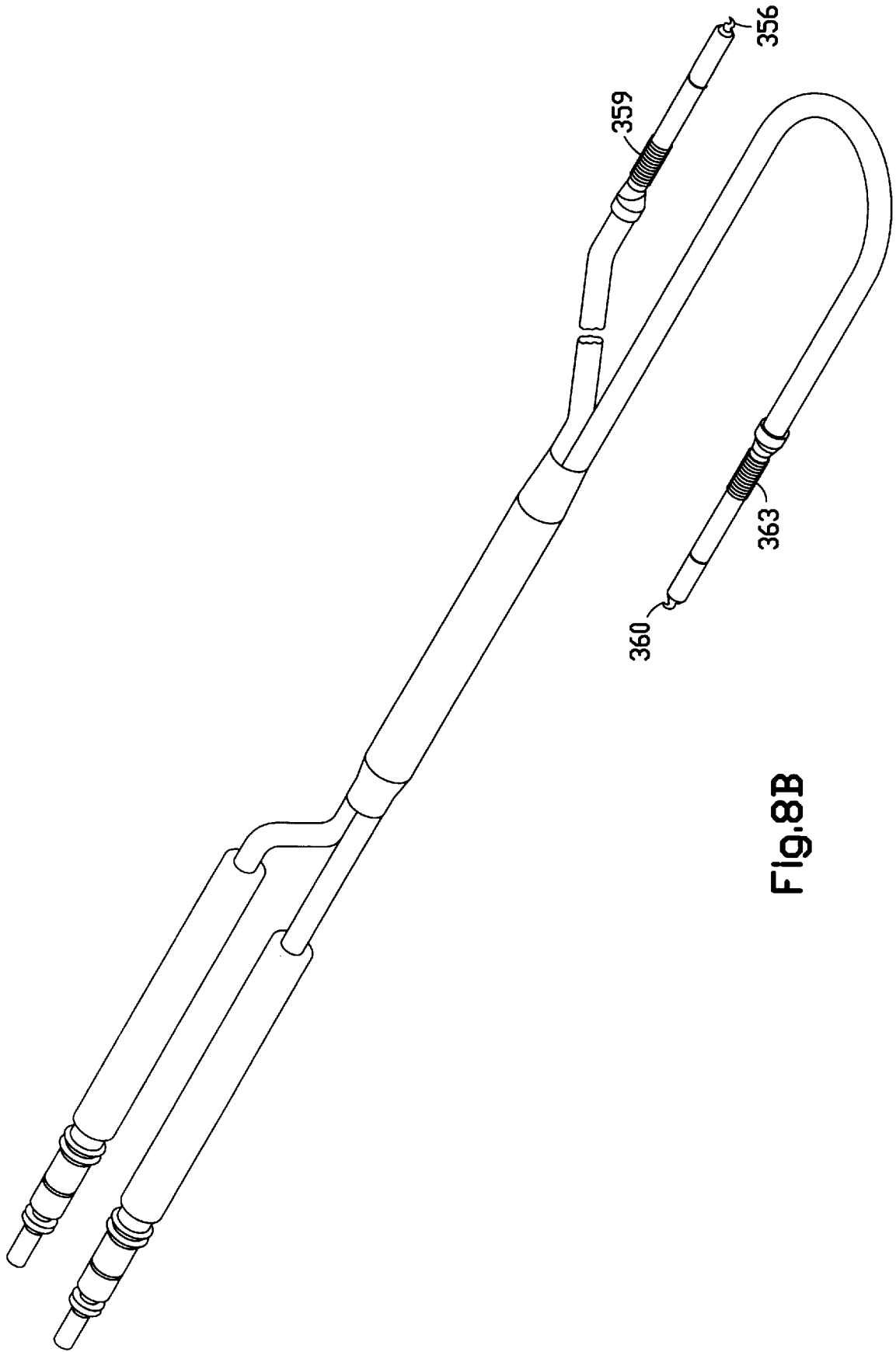
FIG. 8B is a second perspective view illustrating a single-pass lead constructed in accordance with one embodiment of the present invention.

At a distal bifurcation point 309, an intermediate portion 306 of the lead body 320 transitions into two bi-lumen tubes 350, including a first electrode leg 352 and a second electrode leg 354. The first electrode leg 352 and the second electrode leg 354 each extend to the first electrode assembly 310 and the second electrode assembly 312, respectively. A first conductor set is disposed within the first electrode leg 352 and comprises, in one embodiment, a coil and a cable which terminate in a first pacing tip 356 and a first pacing ring 358, respectively. Similarly, a second conductor set is disposed within the second electrode leg 354 and comprises, in another embodiment, a coil and a cable which terminate in a second pacing tip 360 and a second pacing ring 362, respectively. In another embodiment, as shown in FIG. 8B, the first conductor set and the second conductor set disposed within the first electrode leg 352 and the second electrode leg 354, respectively, terminate in a first pacing tip 356 and a first defibrillator electrode 359 second pacing tip 360 and a second defibrillator electrode 363.

The first electrode leg 352 and the second electrode leg 354, in one embodiment, comprise bipolar lead legs. In another embodiment, the first electrode leg 352 is unipolar and the second electrode leg 354 is bipolar (See FIG. 1B). In yet another embodiment, the first electrode leg 352 is bipolar and the second electrode leg 354 is unipolar. The electrode, for either the bipolar or unipolar embodiments of the first and second electrode assemblies 310, 312, comprises a tip electrode, a ring electrode, a defibrillator coil, or their equivalents. The various electrodes can be interchanged and used for pacing, sensing, defibrillating, or a combination of the same.

The second electrode leg 354 has a J-shape, which can have either passive or active fixation. In one embodiment, the active fixation comprises that shown in FIGS. 5 and 6 and discussed above. Using a straight stylet (not shown) to straighten the electrode leg 354 prior to implant, the second electrode leg 354 is positioned within the right atrium of the heart. As the stylet (not shown) is removed, the second electrode leg 354 re-assumes the J-shape and becomes positioned within the atrium of the heart. If a passive configuration is used (FIG. 7), the distal end 355 of the second electrode leg 354 becomes embedded within the wall of the heart as tissue in-growth begins. If an active fixation configuration is used, the distal end 355 of the second electrode leg 354 is positioned adjacent the wall of the heart. The fixation helix is advanced so that it screws into the wall of the heart and the second electrode leg 312 is engaged.

FIG. 9 illustrates another embodiment, showing a view of a lead 400 adapted for delivering electrical pulses to stimulate the heart. The lead 400 has a lead body 420 which extends from a proximal end 402, which is adapted to connect with equipment which supplies electrical pulses, to a distal end 404 which is adapted to be inserted into the heart. The lead body 420 includes an intermediate portion 406 which includes quad-lumen tubing as discussed above. Proximate to the distal end 404 is a first electrode tip 430 including a first electrode assembly 434. A second electrode tip 432 is also provided, as discussed above, which includes a second electrode assembly 436.

Proximate to the proximal end 402 of the lead 400 are connector terminals 410. The connector terminals 410 electrically connect the various electrodes and conductors within the lead 400 to a pulse generator and signal sensor 440. The pulse sensor and generator 440 contains electronics to sense various electrical signals of the heart and also produce current pulses for delivery to the heart, depending on the type of lead 400 used. The pulse sensor and generator 440 also contains electronics and software necessary to detect certain types of arrhythmias and to correct for them. The lead terminal connector 410 provides for the electrical connection between the lead 400 and the pulse generator 440.

To implant the lead 400 within a patient, a single sheath can be used for the single electrode 400 to implant the lead 400 within the heart, which prevents unnecessary trauma to the patient. The first electrode assembly 434 is advanced into the ventricular portion 462 of the heart 460. The first electrode assembly 434 is secured to the ventricle heart 460 using either passive or active fixation. In one embodiment, the active fixation elements are advanced using the terminal pins 134, 136 (FIG. 1). In another embodiment, the active fixation elements are advanced using a stylet (not shown).

The second electrode assembly 436 is advanced, in one embodiment, into the atrium portion 353 of the heart 460 using a straight stylet (not shown). To secure the second electrode assembly 436 into the atrium, the straight stylet is removed and a J-shaped stylet (not shown) is insert into the second electrode assembly 436 and the second electrode assembly 436 takes on the J-shape.

Alternatively, the second electrode assembly 436 is placed within the atrium portion 464 using a J-shaped lead, as shown and discussed above in FIG. 8.

Similar to the first electrode assembly, the second electrode assembly 436 is secured to the heart 460 using either passive or active fixation.

Advantageously, the single pass lead allows for two chambers of the heart to be paced and/or sensed, while only one lead is implanted within the patient. This assists in preventing added stress and expense for the patient. In addition, the active fixation element will not hook nor snag tissue when it is retracted within the lead. The active fixation element also does not require the use of a stylet, since the terminal pins are used to extend and retract the active fixation element. The active fixation allows for the lead to be positioned almost anywhere in the atrium. The movement assembly assists in protecting the shape of the helix even when the helix is under tension.

It is to be understood that the above description is intended to be illustrative, and not restrictive. Many other embodiments will be apparent to those of skill in the art upon reading and understanding the above description. For example, the present invention can be used with a variety of medical devices. Although the use of the lead has been described for use in a cardiac pacing system, the lead could also be applied to other types of body stimulating systems. The scope of the invention should, therefore, be determined with reference to the appended claims, along with the full scope of equivalents to which such claims are entitled.

What is claimed is:

1. A bifurcated lead adapted for implantation in, on or about a heart, the lead comprising:
    a main lead body adapted to carry signals to and from the heart, the main lead body extending from a proximal end to a distal end, the distal end of the main lead body having a first electrode leg and a second electrode leg;
    the first electrode leg including a first electrode assembly comprising a bipolar electrode having a first electrode and a second electrode, the first electrode assembly being adapted to be disposed within a first chamber of the heart;
    the second electrode leg including a second electrode assembly, the second electrode assembly comprising a bipolar electrode having a third electrode and a fourth electrode, the second electrode assembly being adapted to be disposed within a second chamber of the heart; and
    wherein at least the first electrode assembly or the second electrode assembly includes a retractable active fixation device coupled with a mesh screen, the mesh screen coupled with the fixation device such that the fixation device and the mesh screen advance together as the active fixation device is advanced relative to the main lead body towards a portion of the heart wall, where the mesh screen is adapted for contacting a portion of the heart.

2. The lead as recited in claim 1, wherein the lead body has an intermediate portion comprising a quad lumen body.

3. The lead as recited in claim 2, further comprising a yoke coupling the first electrode leg and the second electrode leg with the intermediate portion.

4. The lead as recited in claim 1, wherein the first electrode leg and the second electrode leg each have an elliptical profile.

5. The lead as recited in claim 4, further comprising a dissolvable substance disposed between the first electrode leg and the second electrode leg.

6. The lead as recited in claim 1, wherein the active fixation device is covered with a dissolvable material adapted to protect a patient during lead positioning.

7. The lead as recited in claim 1, further comprising a medication distribution member disposed proximate to the mesh screen.

8. The lead as recited in claim 1, wherein the first electrode assembly has a J-shape.

9. A bifurcated lead adapted for implantation in, on or about a heart, the lead comprising:
    a main lead body adapted to carry signals to and from the heart, the main lead body extending from a proximal end to a distal end, the distal end of the main lead body having a first electrode leg and a second electrode leg;
    the first electrode leg including a first electrode assembly comprising a bipolar electrode having a first electrode and a second electrode, the first electrode assembly being adapted to be disposed within a first chamber of the heart;
    the second electrode leg including a second electrode assembly, the second electrode assembly being adapted to be disposed within a second chamber of the heart; and
    a dissolvable substance disposed between the first electrode leg and the second electrode leg; the dissolvable substance adapted to temporarily couple the first electrode leg with the second electrode leg.

10. A system for monitoring or stimulating cardiac activity, the system comprising:
    a single pass, dual chamber, bifurcated lead adapted for implantation on or about the heart, the lead comprising:
        a main lead body adapted to carry signals to and from the heart, the main lead body extending from a proximal end to a distal end, the distal end of the main lead body having a first leg and a second leg;
        the first leg including a first electrode assembly comprising a bipolar electrode having an active fixation portion, the first electrode assembly comprising a first electrode and a second electrode, the first electrode assembly adapted to be housed within a first chamber of the heart;

the second leg including a second electrode assembly associated with the main lead body, the second electrode assembly comprising a bipolar electrode having an active fixation portion, the second electrode assembly comprising a third electrode and a fourth electrode, the second electrode assembly being housed within a second chamber of the heart;

wherein at least the first electrode assembly or the second electrode assembly includes a retractable active fixation device coupled with a mesh screen, the mesh screen coupled with the fixation device such that the fixation device and the mesh screen advance together as the active fixation device is advanced relative to the main lead body towards a portion of the heart wall; and a signal generator adapted for producing pulses to apply to the heart.

11. A bifurcated lead adapted for implantation in, on or about a heart, the lead comprising:

a main lead body adapted to carry signals to and from the heart, the main lead body extending from a proximal end to a distal end, the distal end of the main lead body having a first electrode leg and a second electrode leg;

the first electrode leg including a first electrode assembly comprising a bipolar electrode having a first electrode and a second electrode, the first electrode assembly being adapted to be disposed within a first chamber of the heart; and the second electrode leg including a second electrode assembly, the second electrode assembly comprising a bipolar electrode having a third electrode and a fourth electrode, the second electrode assembly being adapted to be disposed within a second chamber of the heart, wherein the first electrode leg and the second electrode leg each have an elliptical profile.

12. The lead as recited in claim 11, wherein at least the first electrode assembly or the second electrode assembly further comprises an active fixation device.

13. The lead as recited in claim 12, wherein the active fixation device comprises a helical screw.

14. The lead as recited in claim 12, further comprising a mesh screen adapted for contacting a wall portion of the heart.

15. The lead as recited in claim 12, wherein the active fixation device is retractable.

16. The lead as recited in claim 15, further comprising a mesh screen adapted for contacting a wall portion of the heart, the mesh screen being coupled with the fixation device such that the fixation device and the mesh screen advance together as the active fixation device is retracted.

17. The lead as recited in claim 11, wherein at least the first electrode assembly or the second electrode assembly comprises a passive fixation device.

18. The lead as recited in claim 17, wherein the passive fixation device comprises a plurality of tines disposed proximate to a distal tip of the electrode assembly.

19. The lead as recited in claim 11, further comprising a dissolvable substance disposed between the first electrode leg and the second electrode leg.

20. The lead as recited in claim 11, further comprising a yoke coupling the first electrode leg and the second electrode leg with the intermediate portion.

21. The lead as recited in claim 11, wherein the active fixation device is covered with a dissolvable material adapted to protect a patient during lead positioning.

22. The lead as recited in claim 11, further comprising a medication distribution member disposed proximate to the mesh screen.

23. The lead as recited in claim 11, wherein the first electrode assembly has a J-shape.

24. A bifurcated lead adapted for implantation in, on or about a heart, the lead comprising:

a main lead body adapted to carry signals to and from the heart, the main lead body extending from a proximal end to a distal end, the distal end of the main lead body having a first electrode leg and a second electrode leg;

the first electrode leg including a first electrode assembly comprising a bipolar electrode having a first electrode and a second electrode, the first electrode assembly being adapted to be disposed within a first chamber of the heart; and the second electrode leg including a second electrode assembly, the second electrode assembly comprising a bipolar electrode having a third electrode and a fourth electrode, the second electrode assembly being adapted to be disposed within a second chamber of the heart; and a dissolvable substance disposed between the first electrode leg and the second electrode leg.

25. The lead as recited in claim 24, wherein the lead body has an intermediate portion comprising a quad lumen body.

26. The lead as recited in claim 24, further comprising a yoke coupling the first electrode leg and the second electrode leg with the intermediate portion.

27. The lead as recited in claim 24, wherein at least the first electrode assembly or the second electrode assembly further comprises an active fixation device.

28. The lead as recited in claim 27, wherein the active fixation device is covered with a dissolvable material adapted to protect a patient during lead positioning.

29. The lead as recited in claim 24, further comprising a mesh screen adapted for contacting a wall portion of the heart.

30. The lead as recited in claim 24, wherein at least the first electrode assembly or the second electrode assembly further comprises a retractable active fixation device, and a mesh screen is coupled with the fixation device such that the fixation device and the mesh screen advance together as the active fixation device is retracted.

31. A bifurcated lead adapted for implantation in, on or about a heart, the lead comprising:

a main lead body adapted to carry signals to and from the heart, the main lead body extending from a proximal end to a distal end, where an intermediate portion is disposed therebetween, the intermediate portion comprising quad-lumen tubing;

the distal end of the main lead body having a first leg and a second leg proximate thereto, the proximal end having a first terminal leg and a second terminal leg proximate thereto;

the first leg including a first electrode assembly comprising a bipolar electrode having an active fixation portion, the first electrode assembly comprising a first electrode and a second electrode; the first electrode assembly adapted to be disposed within a first chamber of the heart; and the second leg including a second electrode assembly associated with the main lead body, the second electrode assembly comprising a bipolar electrode having an active fixation portion, the second electrode assembly comprising a third electrode and a fourth electrode, the second electrode assembly adapted to be disposed within a second chamber of the heart.

* * * * *